(12) United States Patent
Hoffer et al.

(10) Patent No.: US 8,428,749 B2
(45) Date of Patent: Apr. 23, 2013

(54) NERVE CUFF, METHOD AND APPARATUS FOR MANUFACTURING SAME

(75) Inventors: Joaquin Andres Hoffer, Village of Anmore (CA); Marc-Olivier Imbeau, Saint-Augustin-de-Desmaures (CA); Jean-Martin Vallieres, Quebec (CA)

(73) Assignee: Neurostream Technologies General Partnership, Quebec (CA)

( * ) Notice: Subject to any disclaimer, the term of this patent is extended or adjusted under 35 U.S.C. 154(b) by 0 days.

(21) Appl. No.: 13/486,864

(22) Filed: Jun. 1, 2012

(65) Prior Publication Data
US 2012/0233855 A1  Sep. 20, 2012

Related U.S. Application Data

(62) Division of application No. 11/809,934, filed on Jun. 4, 2007, now Pat. No. 8,214,056.

(60) Provisional application No. 60/810,130, filed on Jun. 2, 2006.

(51) Int. Cl.
*A61N 1/00* (2006.01)

(52) U.S. Cl.
USPC .......................................................... 607/118

(58) Field of Classification Search .................. 607/118; 264/259, 271.1, 279.1, 229
See application file for complete search history.

(56) References Cited

U.S. PATENT DOCUMENTS

| | | | |
|---|---|---|---|
| 4,602,624 A | 7/1986 | Naples et al. | |
| 5,400,784 A | 3/1995 | Durand et al. | |
| 5,634,462 A | 6/1997 | Tyler et al. | |
| 5,824,027 A | 10/1998 | Hoffer et al. | |
| 5,919,220 A | 7/1999 | Stieglitz et al. | |
| 2003/0040785 A1 | 2/2003 | Maschino et al. | |
| 2005/0010265 A1 | 1/2005 | Baru Fassio et al. | |
| 2006/0030919 A1 | 2/2006 | Mrva et al. | |

FOREIGN PATENT DOCUMENTS

| | | |
|---|---|---|
| CA | 2266999 A1 | 9/2000 |
| EP | 1 001 827 B1 | 5/2000 |

OTHER PUBLICATIONS

Loeb et al. "Cuff electrodes for chronic stimulation and recording of peripheral nerve activity", Journal of Neuroscience Methods, 1996, pp. 95-103, vol. 64.

*Primary Examiner* — Carl H Layno
*Assistant Examiner* — Paula J Stice
(74) *Attorney, Agent, or Firm* — Polsinelli Shughart PC (57) ABSTRACT

A nerve cuff comprising a wall band member having an inner surface defining a lumen when the wall band member is in a closed configuration for receiving a nerve therethrough. At least one longitudinal and contiguous conductor extends within the lumen. The conductor is insulated and has at least one exposed portion thereby providing an electrode. When mounting the nerve cuff to a nerve, each electrode is in electrical communication with the nerve. A multi-channel nerve cuff further comprises a plurality of longitudinal ridges formed on the inner surface with each adjacent pair of ridges defining a longitudinal chamber. Each chamber comprises a respective conductor extending therein. When mounting the multi-channel nerve cuff to the nerve, the ridges abut the nerve providing for each chamber to isolate respective longitudinal portions of the nerve. A method and an apparatus for manufacturing such nerve cuffs are also disclosed.

18 Claims, 11 Drawing Sheets

NERVE CUFF, METHOD AND APPARATUS FOR MANUFACTURING SAME

CROSS-REFERENCE TO RELATED APPLICATIONS

This application is a Divisional Application of U.S. Pat. No. 8,214,056 filed Jun. 4, 2007, which claims priority from U.S. Provisional Application Ser. No. 60/810,130 filed Jun. 2, 2006, both of which are hereby incorporated by reference in their entirety.

FIELD OF THE INVENTION

The present invention relates to a nerve cuff for stimulating and monitoring electrical activity in nerve tissues in human beings and other creatures possessing a nervous system. The present invention also relates to method and apparatus for manufacturing a nerve cuff.

BACKGROUND OF THE INVENTION

Various types of cuff transducers intended for use as electrical or chemical interfaces with neural tissue have been described in the literature. These nerve cuffs typically have a tubular bio-compatible dielectric material wall. In nerve cuffs designed to provide an electrical interface to tissues inside the nerve cuff, the inside of the nerve cuff wall supports one or more metal electrodes. Leads from the electrodes extend through and are supported by the nerve cuff wall. The nerve cuff walls must be sufficiently rigid to support the leads and electrodes. The leads may be connected to suitable signal-conditioning devices or electrical stimulation devices.

Nerve cuff electrodes have been used in stimulation systems with the goal of providing partial voluntary control of muscles that have been paralyzed as a result of lesions caused by spinal cord injury, stroke, or other central neurological system disorders. In some cases, partial motor function may be restored by stimulating motor neurons or muscles below the level of the lesion. Nerve cuffs may also be used as sources for the measurement of the neurological signal of the peripheral nervous system and for feedback of closed-loop functional electrical stimulation (FES) systems.

As such, there is increasing interest in the use of nerve cuffs to preferentially monitor and/or stimulate activity in selected axons within a nerve bundle. Hoffer et al., U.S. Pat. No. 5,824,027, which is incorporated herein by reference in its entirety, describes a multi-channel nerve cuff having longitudinal ridges extending along the interior walls of the nerve cuff.

The ridges divide the volume between the nerve cuff wall and the tissues within the nerve cuff into separate chambers. Electrodes are located in the chambers. This cuff structure can provide improved nerve signal recording selectivity and enhanced stimulation selectivity as compared to conventional nerve cuffs which lack separate chambers.

Fabricating a multi-chamber, multi-channel nerve cuff having one or more independent electrodes in each of several chambers is challenging, especially where the cuff is small in size. It is frequently desirable to provide nerve cuffs having internal diameters of only 2-3 mm. The challenge is compounded by the fact that such cuffs should be fabricated from material which is sufficiently flexible to minimize damage to delicate neural tissue, such as may occur with compression, sharp bending and/or stretching of the tissue. Suitable materials, such as bio-compatible silicone compositions may stretch when they are manipulated. This flexibility in the nerve cuff wall may make it difficult to place electrodes in precisely determined locations and to keep the electrodes in position.

Tyler, et al., U.S. Pat. No. 5,634,462, which is incorporated herein by reference in its entirety, describes multi-channel nerve cuffs constructed of stiff material. The Tyler et al. nerve cuffs are designed to deform and even penetrate a nerve, with the objective off approximating electrodes to more centrally located axons in nerves. A problem with this type of device is the possibility that the nerve could be damaged by the nerve cuff.

There is a need for methods to more readily accurately fabricate multi-channel nerve cuffs. Nerve cuffs used for making recordings of electrical activity within nerve tissues should provide good electrical isolation of the tissues within the nerve cuffs. There is also a need for nerve cuffs which may provide better isolation from externally generated electrical noise than is provided by current cuff designs. There is further needed a nerve cuff that may be used effectively to selectively stimulate or record from targeted subpopulations of nerve fibers in a nerve and may be used on nerves which could be damaged by penetration.

OBJECTS OF THE INVENTION

An object of the present invention is to provide a nerve cuff.

Another object of the present invention is to provide a multi-channel nerve cuff.

A further object of the present invention is to provide a method of manufacturing a nerve cuff.

Another object of the present invention is to provide an apparatus for manufacturing a nerve cuff.

SUMMARY OF THE INVENTION

In accordance with an aspect of the present invention there is provided a method of manufacturing a nerve cuff. The method includes providing a mold containing a plurality of longitudinal grooves, positioning one of a plurality of longitudinal conductors coated with insulation within each longitudinal groove, applying flexible bio-compatible material on the mold with the plurality of longitudinal conductors positioned therein, and curing the flexible bio-compatible material so as to provide a wall band member adhered to the plurality of longitudinal conductors. The method further includes ejecting the wall band member with the adhered longitudinal conductor and removing at least one portion of the insulation on the plurality of longitudinal conductors to provide electrodes. Each of the at least one removed portions is situated between a proximal end and a distal end of each longitudinal conductor.

Other objects, advantages and features of the present invention will become more apparent upon reading of the following non-restrictive description of illustrative embodiments thereof, given by way of example only with reference to the accompanying drawings.

BRIEF DESCRIPTION OF THE FIGURES

Illustrative embodiments of the invention will be described by way of example only with reference to the accompanying drawings, in which.

DETAILED DESCRIPTION OF THE ILLUSTRATIVE EMBODIMENTS

Generally stated, an implantable interface in the form of a nerve cuff, hereinafter referred to as "nerve cuff", according to an illustrative embodiment of the present invention is used for stimulating and/or monitoring electrical activity in nerve tissues in human beings or other creatures possessing nervous systems. The interface may have particular application in functional electrical stimulation ("FES") of the neuromuscular system.

Figure 1:
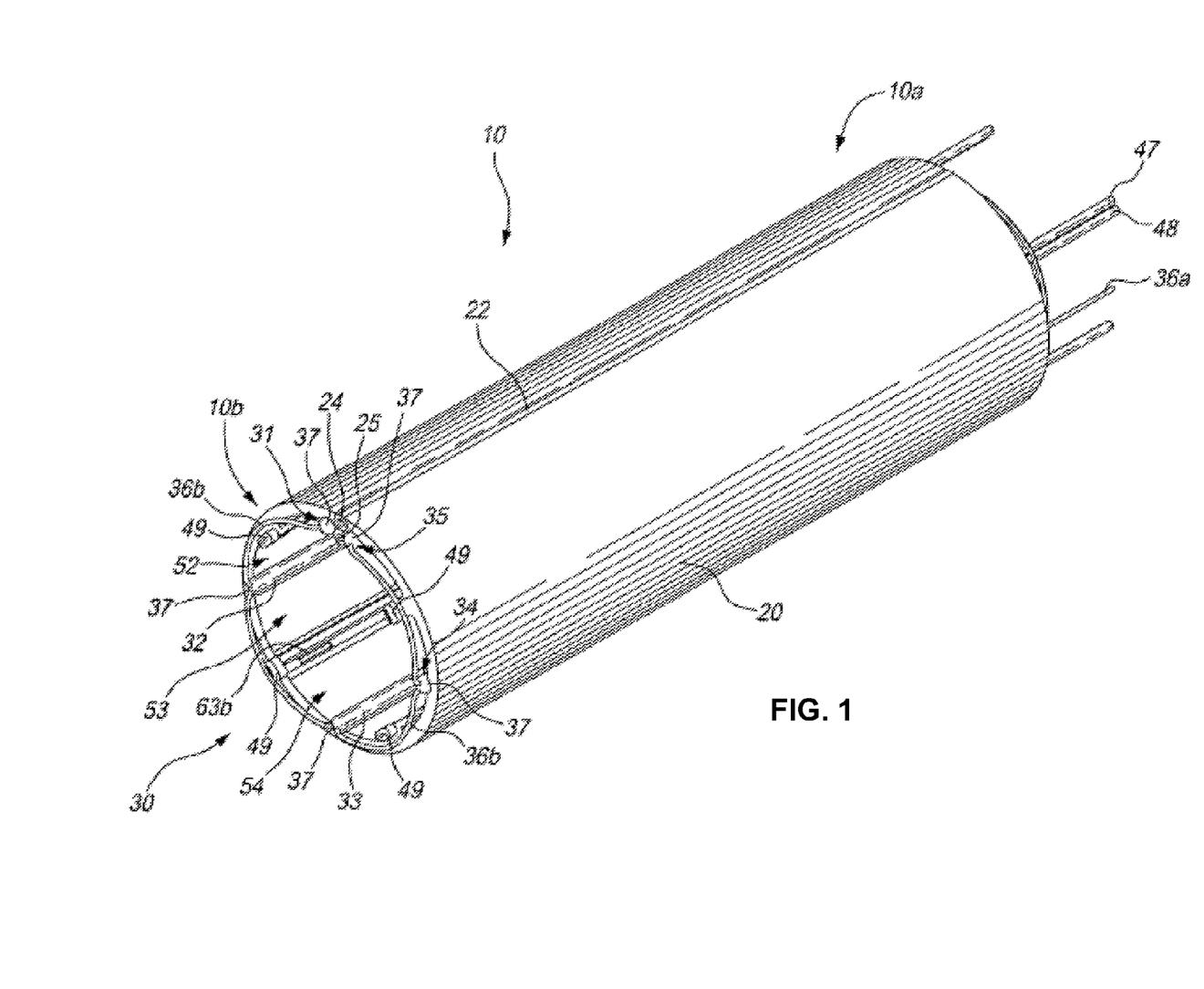
FIG. 1 is a perspective view of a nerve cuff in a closed configuration in accordance with an illustrative embodiment of the present invention.
Figure 2:
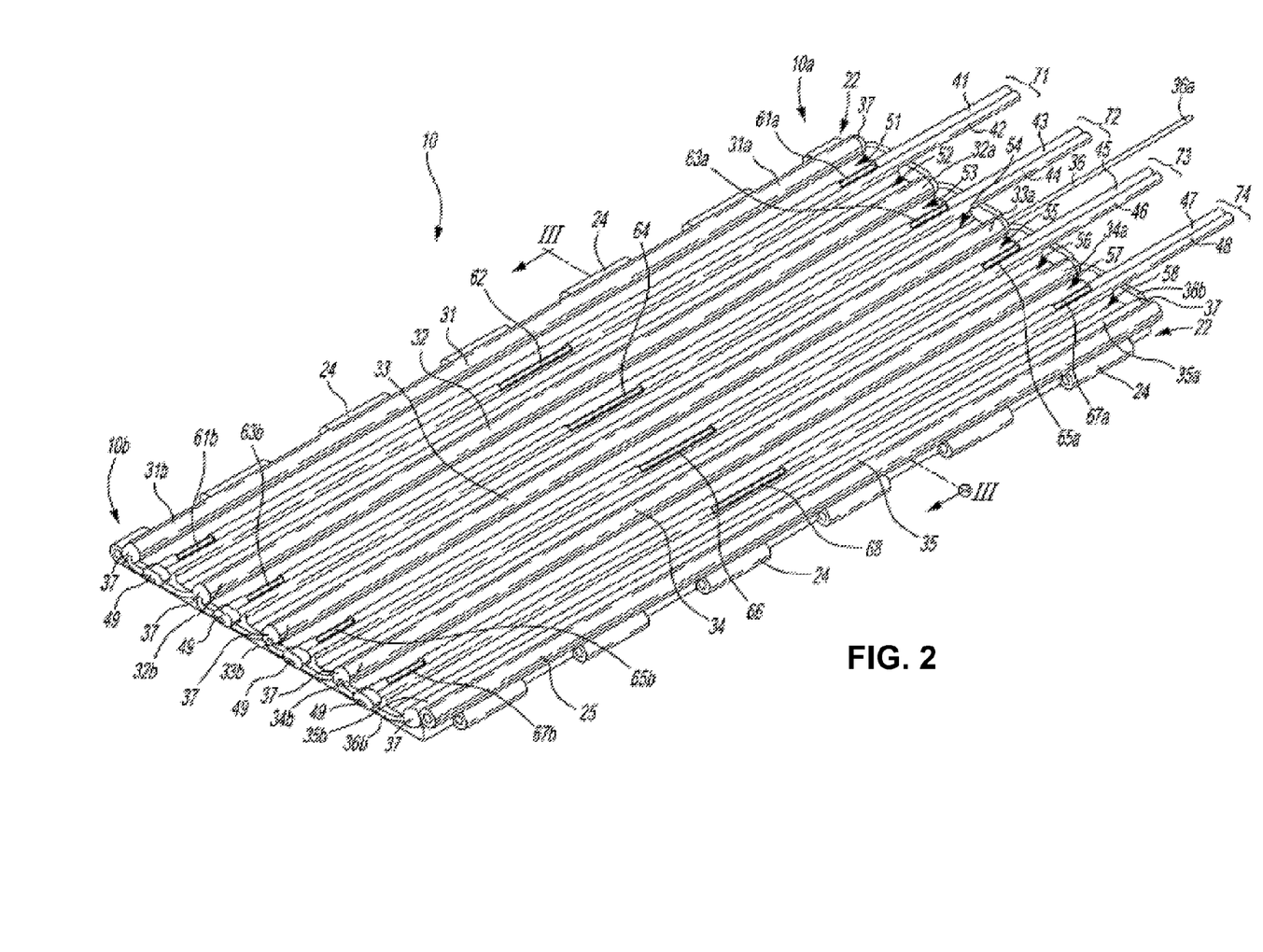
FIG. 2 is a perspective view of the nerve cuff of FIG. 1 in an open configuration.

Referring to FIGS. 1 and 2, there is shown a non-limitative illustrative embodiment of a nerve cuff 10 in a closed configuration (FIG. 1) and in an open configuration (FIG. 2). The nerve cuff 10 has a wall member 20 in the form of a band which has a generally tubular configuration when in a closed configuration, as shown in FIG. 1. This wall band member or wall member 20 defines a lumen 30, when it is in the closed configuration, which is sized to receive a nerve or other bodily tissue. The surface of the wall band member 20 which defines the lumen 30 and which is interfaced to a nerve N (see FIG. 14) is the inner surface of the wall band member 20. A closure 22 allows the nerve cuff 10 to be opened to receive a nerve N (see FIG. 14) or other bodily tissue in lumen 30. Closure 22 may then be closed to isolate the bodily tissue within lumen 30. The closure 22 may be any suitable closure, however, the closure 22 advantageously comprises interdigitating closing elements 24 affixed on either lateral side of the wall band member 20 combined with a sealing tube 25. Closure 22 may be secured in a closed configuration by inserting a rod-like member (not shown) through interdigitated closing members 24.

Five longitudinal ridges 31, 32, 33, 34 and 35 and four longitudinal conductors in the form of pairs of elevated contiguous electrode wires (41, 42), (43, 44), (45, 46) and (47, 48) extending along the inner surface within the lumen 30 delimitate, in alternating disposition, eight chambers 51, 52, 53, 54, 55, 56, 57 and 58, as best seen in FIG. 2. It is to be understood that while the nerve cuff 10 of the illustrative embodiment contains eight chambers 51, 52, 53, 54, 55, 56, 57 and 58, the nerve cuff 10 may have a different number of chambers and/or ridges and/or pairs of elevated electrodes, depending on the application.

The example shown herein is a multi-channel nerve cuff 10, yet nerve cuffs with a single channel can also be provided within the scope of the present invention. It should also be noted that the longitudinal conductors exemplified herein are not limited to pairs of wires but include other suitable conductors known in the art.

Other types of electrodes can also be provided within the scope of the invention. Hence, rather than longitudinal contiguous conductors, short discontinuous conducting elements, whether wires or other elements, can also be contemplated.

Furthermore, in another embodiment, the wall member 20 may have a port (such as an opening) located within one or more of the chambers 51, 52, 53, 54, 55, 56, 57 and 58 so as to allow connection to an agent delivery system for agents such as, for example, a pharmaceutical agent.

Figure 14:
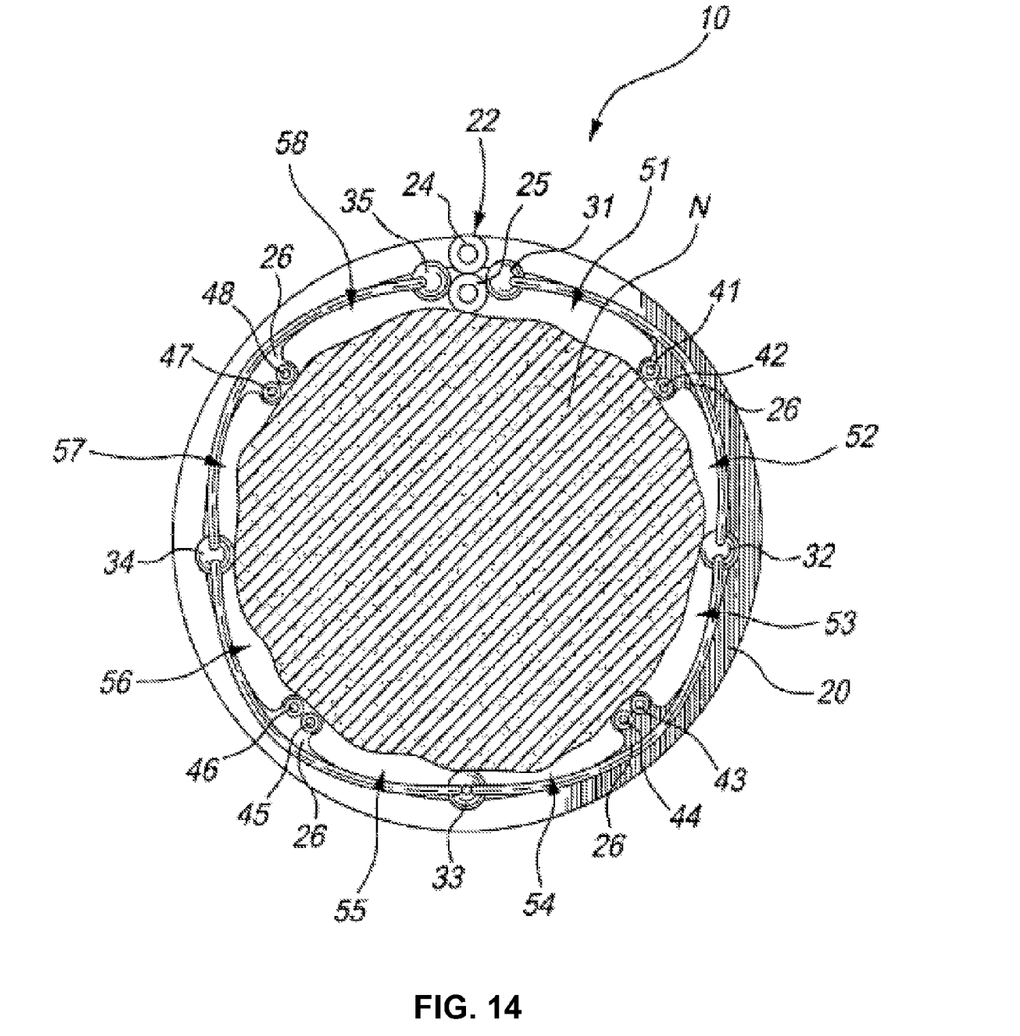
FIG. 14 is a sectional view of the nerve cuff of FIG. 1 mounted on a nerve.

FIG. 14 illustrates the nerve cuff 10 in use mounted to a nerve N and secured thereto via closure 22. The ridges 31, 32, 33, 34 and 35 abut the nerve N, providing for each chamber 54, 55, 56, 57 and 58 to isolate respective longitudinal regions of the nerve N. The electrodes (referenced herein below) are in contact or at least substantially near the nerve N.

In the following description, the specific components used are meant as examples only so as to describe a functional realization of the illustrative embodiment and are not meant to limit the present invention to these specific components.

Wall Member

The wall member 20 may be made by molding implant grade silicone, for example room temperature vulcanizing (RTV) silicone. It is to be understood that other suitable implant grade may be used.

Ridges

The ridges 31, 32, 33, 34 and 35 consist of generally parallel commercial silicone tubing such as, for example, 0.025"×0.012" silicone tubing from Allied Biomedical (AlliedSil™). The ridges 31, 32, 33, 34 and 35 enclose a ground wire 36, which may be fabricated using, for example, a hard temper type of wire such as 316 LVM wire, 1×19×0.0012; 0.006 (Fort Wayne Metals Production Number 72073; Hard temper), with a 0.003" thick ETFE insulation for a total outer diameter of 0.012". The ground wire 36 comprises a lead 36a and a contact section 36b. The ground wire contact section 36b, which is de-insulated, is sequentially passed through the tubing forming the ridges 31, 32, 33, 34 and 35 in a systematic pattern so that the ground wire contact portion 36b is exposed between any two consecutive ridges 31, 32, 33, 34 and 35. As for the ground wire lead 36a, it remains insulated over the entire length from the edge of the nerve cuff 10 to its end for connection to some further interface or device (not shown).

In its suggested routing, the ground wire contact section 36b is first inserted through the proximal end 33a of the middle ridge 33 to its distal end 33b, then goes from the distal end 33b of the middle ridge 33 to the distal end of an adjacent ridge, for example the distal end 32b of ridge 32, to its proximal end 32a. From the proximal end 32a of ridge 32 the ground wire contact section 38b goes to the proximal end 31a of outer ridge 31, to its distal end 31b. From the distal end 31b of ridge 31 the ground wire contact section 36b goes to the distal end 32b of ridge 32, to its proximal end 32a. Finally, from the proximal end 32a of ridge 32 the ground wire contact section 36b goes to the proximal end 33a of middle ridge 33, to its distal end 33b. This crisscross pattern is continued through ridges 34 and 35 until it makes a final pass from the proximal end 33a of the middle ridge 33 to its distal end 33b.

The result is that the middle ridge 33 encloses three passes of the ground wire contact section 36b, the intermediate ridges 32, 34 enclose two passes of the ground wire contact section 36b and the outermost ground wire ridges 31, 35 enclose one pass of the ground wire contact section 36b.

In order to prevent the ends of the ridges 31, 32, 33, 34 and 35 tubing from being deformed, the radius of curvature of the ground wire contact section 36b as it exits the tubing may be approximately 0.8 mm and the contact section 36b may be generally straight between adjacent ridges. A jig can also be used in order to provide for the loops of ground wire to be consistent.

Once the ground wire 36 has been positioned within the ridges 31, 32, 33, 34 and 35, the end of each ridge 31, 32, 33, 34 and 35 is sealed with an adhesive silicone plug 37. The length of the adhesive silicone plug 37 inside each ridge 31, 32, 33, 34 and 35 being generally from about 1.0 mm to 1.5 mm and protruding in a generally dome shape.

Electrodes

The wire used for the electrode wires (41, 42), (43, 44), (45, 46) and (47, 48) may be, for example, a 316 LVM wire, 1×19×0.0012; 0.006 (Fort Wayne Metals Production Number 72073; Hard temper), with a 0.003" thick ETFE insulation (Tempflex) for a total outer diameter of 0.012" or PT_Ir 70-30.

Figure 3:
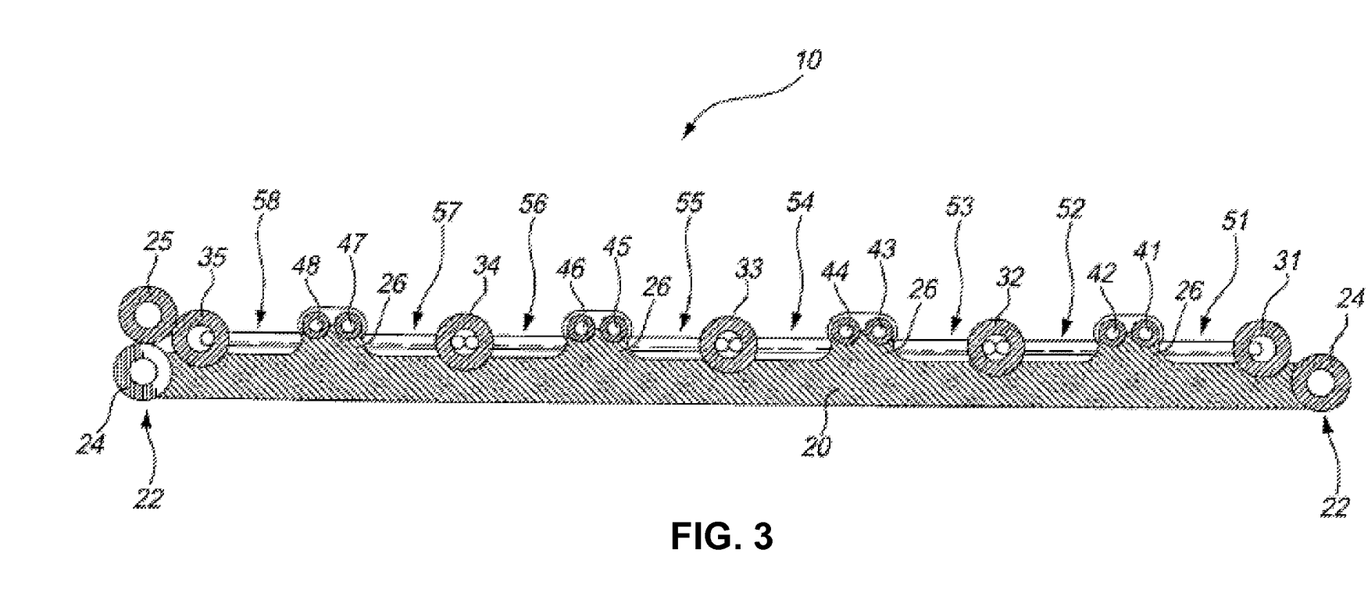
FIG. 3 is a cross sectional view of the nerve cuff taken along the axis of FIG. 2.

As best seen in FIG. 3, the pairs of electrode wires (41, 42), (43, 44), (45, 46) and (47, 48) may be positioned on top of longitudinal protuberances 26, extending along the inner surface into the lumen 30, so as to be generally at the same level as the ridges 31, 32, 33, 34 and 35 relative to the inner surface of the wall band member 20. This elevation with respect to the surface of the wall member 20 allows the electrode wires (41, 42), (43, 44), (45, 46) and (47, 48) to be located at least near the surface of the nerve or to be in contact with the nerve, this diminishes the nerve/electrode impedance and results in higher sensibility to nerve activity.

In another embodiment, the protuberances 26 may be omitted so that the electrode wires (41, 42), (43, 44), (45, 46) and (47, 48) or other conducting elements lay directly upon the surface of the wall member 20. In still another embodiment, the electrode wires (41, 42), (43, 44), (45, 46) and (47, 48) or other conducting elements may be embedded within the protuberances 26, the protuberances 26 may be apertured in order to expose the electrode wires or other conductors. In yet another embodiment, the electrode wires (41, 42), (43, 44), (45, 46) and (47, 48) or other conducting elements are embedded within the wall member 20, with the wall member 20 being apertured in order to expose the electrode wires or other conductors.

Referring back to FIG. 2, the pairs of electrode wires (41, 42), (43, 44), (45, 46) and (47, 48) are used to create electrodes (61a, 61b, 62), (63a, 63b, 64), (65a, 65b, 66) and (67a, 67b, 68), respectively, in "tri-polar" or "quasi-tri-polar" configurations. This means that each electrode channel 71, 72, 73 and 74 comprises two indifferent electrodes (61a, 61b), (63a, 63b), (65a, 65b) and (67a, 67b) and one recording electrode 62, 64, 66 and 68, respectively. The indifferent electrodes (61a, 61b), (63a, 63b), (65a, 65b) and (67a, 67b) may be advantageously positioned symmetrically with respect to the total length of the nerve cuff 10, a first set of indifferent electrodes 61a, 63a, 65a and 67a being located near the proximal end 10a of the nerve cuff 10 and a second set of indifferent electrodes 61b, 63b, 65b and 67b being located near the distal end 10b of the nerve cuff 10. The recording electrodes 62, 64, 66 and 68 may be advantageously located in the center 10c of the nerve cuff 10.

The electrodes (61a, 61b, 62), (63a, 63b, 64), (65a, 65b, 66) and (67a, 67b, 68) may be created by removing part of the ETFE insulation of the corresponding electrode wires (41, 42), (43, 44), (45, 46) and (47, 48). By creating the indifferent electrodes (61a, 61b), (63a, 63b), (65a, 65b) and (67a, 67b) from the same electrode wire 41, 43, 45 and 47 for each corresponding electrode channel 71, 72, 73 and 74, this avoids welding and provides a proper impedance match. The recording electrodes 62, 64, 66 and 68 may be created from the remaining electrode wire 42, 44, 46 and 48 of each corresponding electrode channel 71, 72, 73 and 74. The method used for the creation of the electrodes (61a, 61b, 62), (63a, 63b, 64), (65a, 65b, 66) and (67a, 67b, 68) will be further described later on.

In another alternative embodiment (not shown), the pairs of electrode wires (41, 42), (43, 44), (45, 46) and (47, 48) may be used to create electrodes in "bi-polar" configurations. This means that each electrode channel 71, 72, 73 and 74 comprises one indifferent electrode and one recording electrode. The indifferent electrodes and the recording electrodes may be positioned at opposed ends of the nerve cuff 10. For example, the indifferent electrodes may be located near the proximal end 10a of the nerve cuff 10 and the recording electrodes may be located near the distal 10b end of the nerve cuff 10.

Therefore, a single longitudinal and contiguous conductor such as a pair of insulated wires can be used to provide for one or more electrodes when removing lengths thereof, hence facilitating the manufacturing of such nerve cuffs as well as their efficacy.

Electrode Capping

The electrode wires (41, 42), (43, 44), (45, 46) and (47, 48) are positioned so as to protrude approximately 2.0 mm beyond the wall member 20. The protruding ends of the electrode wires (41, 42), (43, 44), (45, 46) and (47, 48) are covered by RTV silicone forming an electrode cap 49, as may be seen in FIGS. 1, 2 and 4A. However, before the application of the RTV silicone, the outer surface 83 of the ETFE insulation on the protruding end of the electrode wires (41, 42), (43, 44), (45, 46) and (47, 48) is etched to ensure proper bonding of the RTV silicone forming the cap 49.

In another embodiment the electrode wires (41, 42), (43, 44), (45, 46) and (47, 48) may be cut or positioned so as not to protrude beyond the wall member 20 (not shown). In this embodiment, some RTV silicone would flow over the end of the electrode wires (41, 42), (43, 44), (45, 46) and (47, 48) and mainly bond to the exposed inner surface 82 of the ETFE insulation, as shown in FIG. 4B. The issue with this embodiment is that the inner surface 82 of the ETFE insulation may not be etched because the etching solution may migrate to the core 81 of the electrode wires (41, 42), (43, 44), (45, 46) and (47, 48). Thus, the bonding of the RTV silicone to the electrode wires (41, 42), (43, 44), (45, 46) and (47, 48) is not as strong as in the illustrative embodiment. Therefore, the silicone cap 49 could possibly separate from the end of the electrode wires (41, 42), (43, 44), (45, 46) and (47, 48) and allow for the core 81 to be exposed.

Closure

The closure 22 is fabricated from a single length of implant grade commercial silicone tubing, for example AlliedSil™ Tubing 0.012"×0.025". In the illustrative embodiment shown in FIGS. 1 and 2, the tubing is cut into closing elements 24 in the form of tubular links on each side of the nerve cuff 10 to realize a piano hinge interlocking system. The closing elements 24 on one side of the nerve cuff 10 are combined with a sealing tube 25 extending the whole length of the nerve cuff 10. When the nerve cuff 10 is in a closed configuration, as best seen in FIG. 1, the sealing tube 25 rests right under the closure 22 filling the space between outer ridges 31 and 35, effectively creating a seal preventing bodily fluids from passing through the closure 22. As mentioned previously, the closure 22 may be secured in the closed configuration by inserting a rod-like member, for example a standard permanent polypropylene suture wire, through the interdigitated closing members 24.

It is to be understood that the sealing tube 25 may be any other suitable sealing means bridging the gap between outer ridges 31 and 35, or may be filled instead of hollow.

Cuff Width, Nerve Circumference, Ridge and Closing Members Tubing Diameter Relation For a single nerve cuff 10, Equation 1 shows the relationship between nerve cuff width (W), nerve circumference (NC), ridge tubing diameter ((pRT) and closing members tubing diameter (CE).

$$NC=W+4.1416\ CE-6.28320T-2.3939\ mm. \qquad \text{Equation 1}$$

Manufacturing

Figure 5:
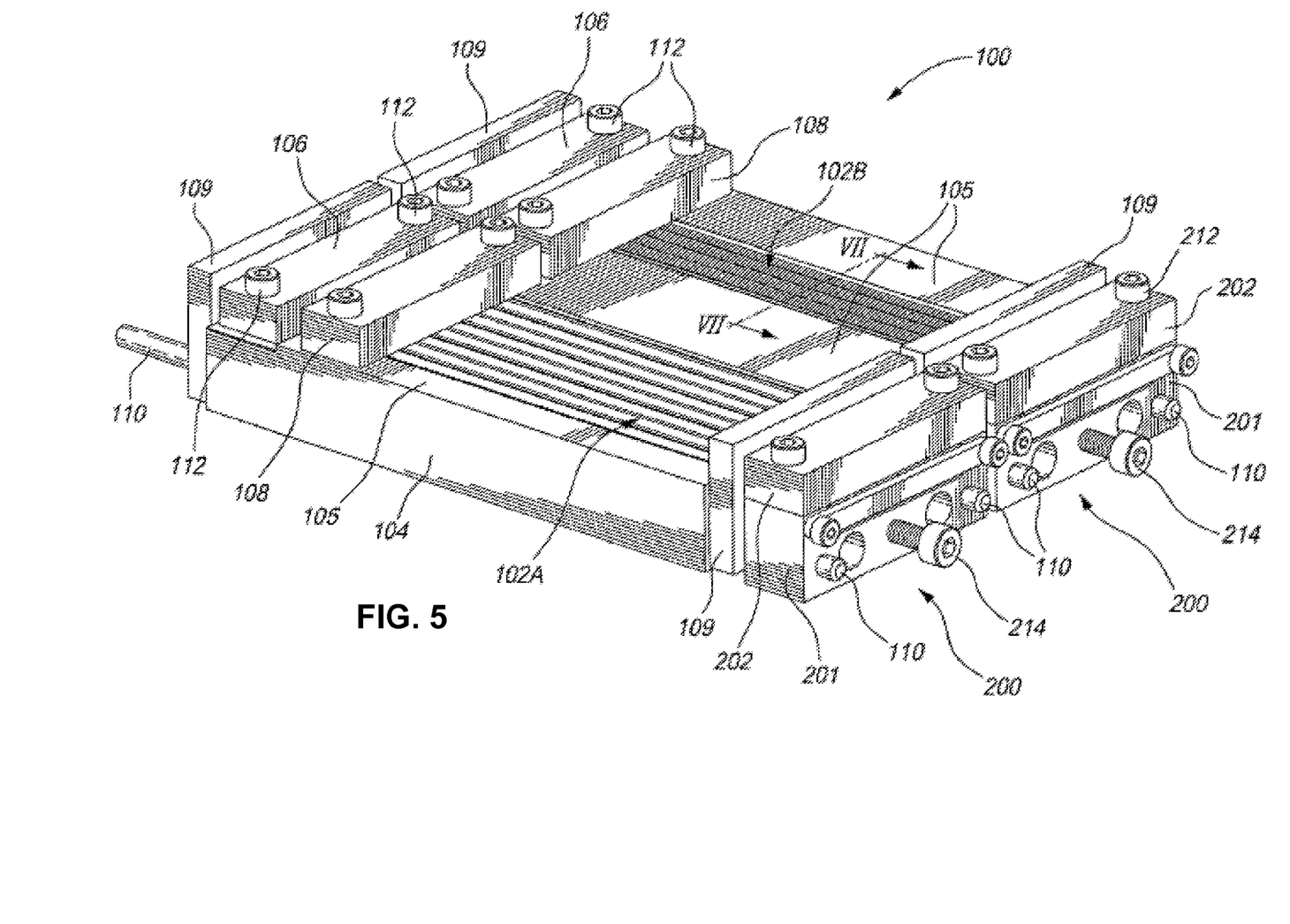
FIG. 5 is a perspective view of an apparatus for manufacturing a nerve cuff in accordance with an illustrative embodiment of the present invention.
Figure 6:
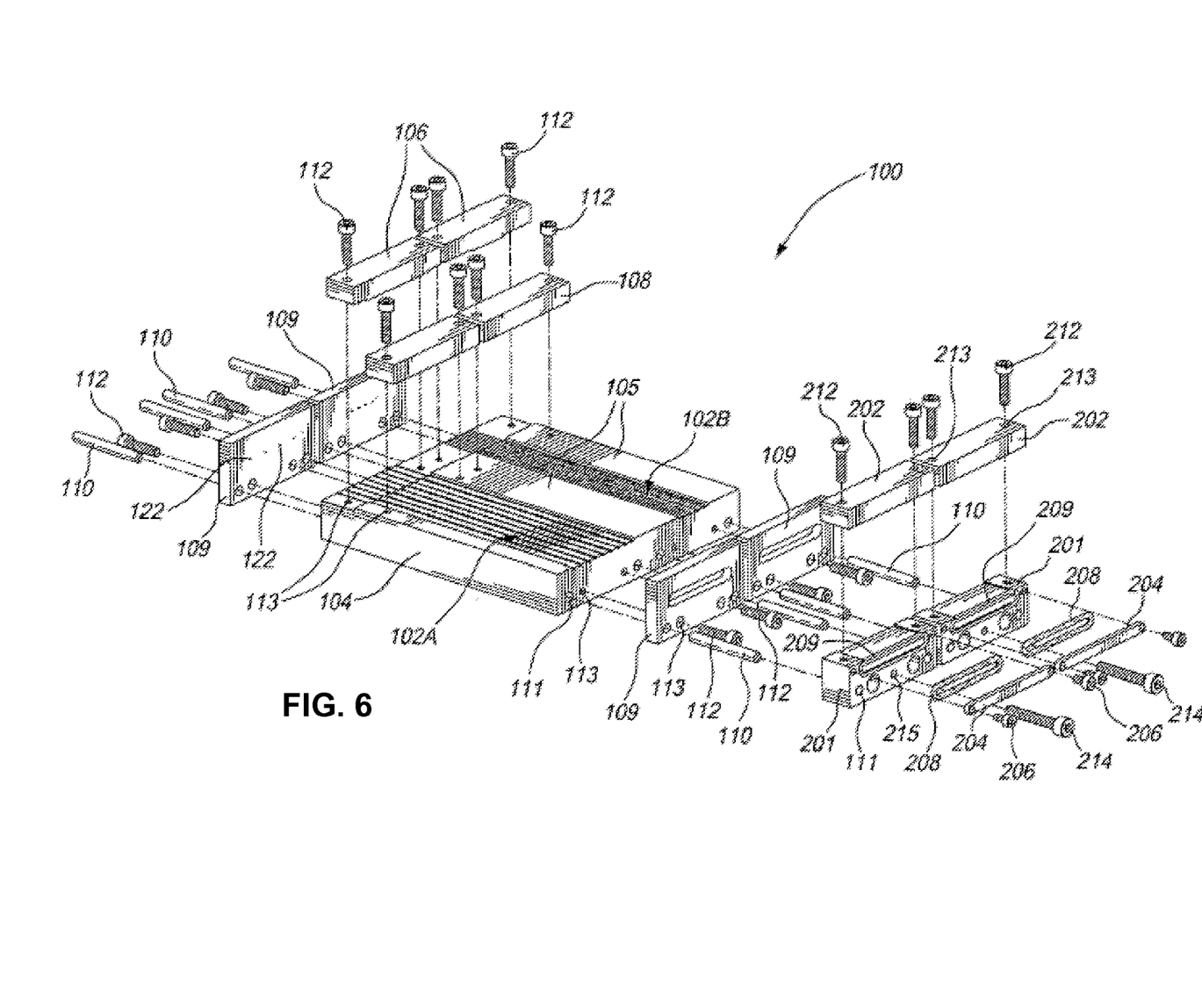
FIG. 6 is an exploded perspective view of the apparatus of FIG. 5.

The nerve cuff 10 may be manufactured using a cast silicone process performed in an apparatus 100 for manufacturing a nerve cuff having open molds 102A and 102B, as shown in FIGS. 5 and 6. Although the illustrated embodiment of the molding apparatus 100 shows two molds 102A and 102B, it is to be understood that the molding apparatus 100 may have a single mold or more than two molds.

The molds 102A and 102B are formed within the top face of a base 104 on which are operatively connected electrode wire clamps 106, tubing clamps 108, end plates 109 and tightness adjustment mechanisms 200. Guiding members 110, which are inserted into guiding slots 111, are used to properly align the end plates 109 and tightness adjustment mechanisms 200 to base 104, while securing members 112 interact with securing slots 113 to secure the electrode wire clamps 106, the tubing clamps 108 and the end plates 109 to the base 104.

A coating is applied to the molds 102A and 102B to prevent the RTV Silicone from bonding to the molds 102A and 102B. The coating may be, for example, a one time spray-on baked finish Teflon coating (ProteKote 840) by Pro-Tek Coatings or Poly-Ond by Polycoatings. The coating may be, for example a spray-on baked finish as PFA coating (420-703 Primer and 857-210 Topcoat) by Dupont or Liquid bath process deposition (Poly-Ond by Polycoatings) to give but a few examples.

Figure 7:
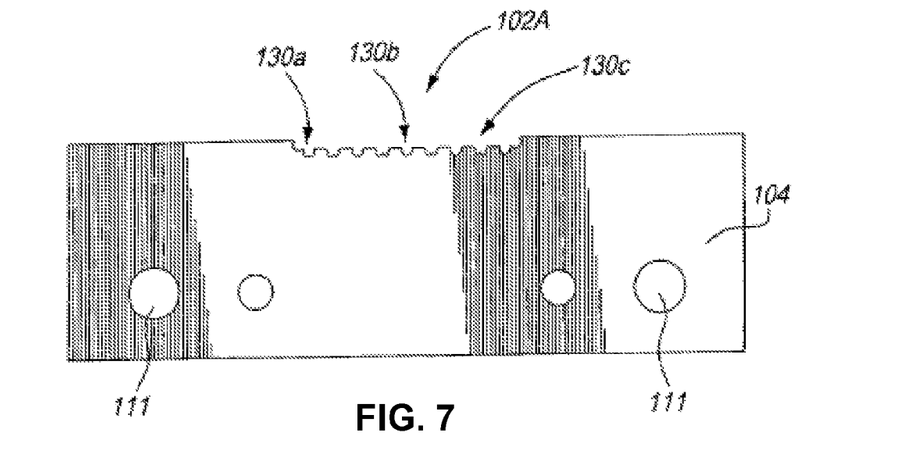
FIG. 7 is cross sectional view of the apparatus taken along axis VII-VII of FIG. 5.
Figure 8:
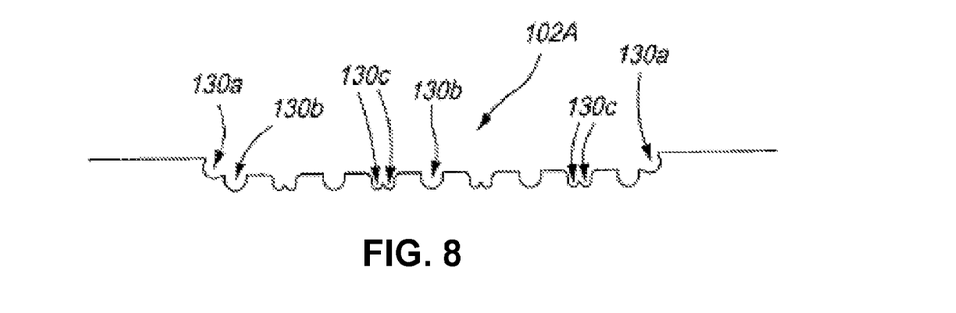
FIG. 8 is a detailed view of FIG. 7.

Referring to FIGS. 7 and 8, the molds 102A and 102B grooves 130 may be created in the base 104 using wire electric discharge machining (EDM) or high speed CNC machining. The grooves 130 serve to properly retain the silicone tubes 24, 31, 32, 33, 34 and 35 and electrode wires 41, 42, 43, 44, 45, 46, 47 and 48 during the molding process. The two grooves 130a that retain the closing elements 24 tubing are not as deep as the ridges 31, 32, 33, 34 and 35 tubing grooves 130b and the electrode wires 41, 42, 43, 44, 45, 46, 47 and 48 grooves 130c due to the cuff geometry.

Figure 9:
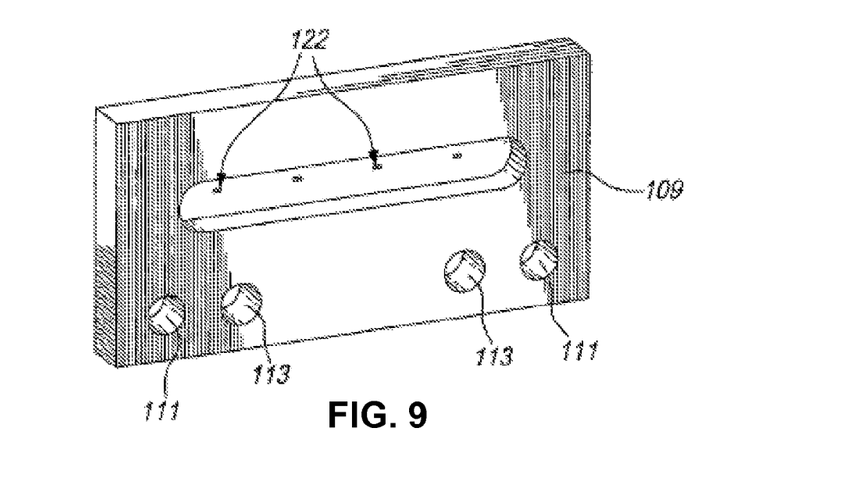
FIG. 9 is a perspective view of an end plate of the apparatus of FIG. 5.
Figure 13:
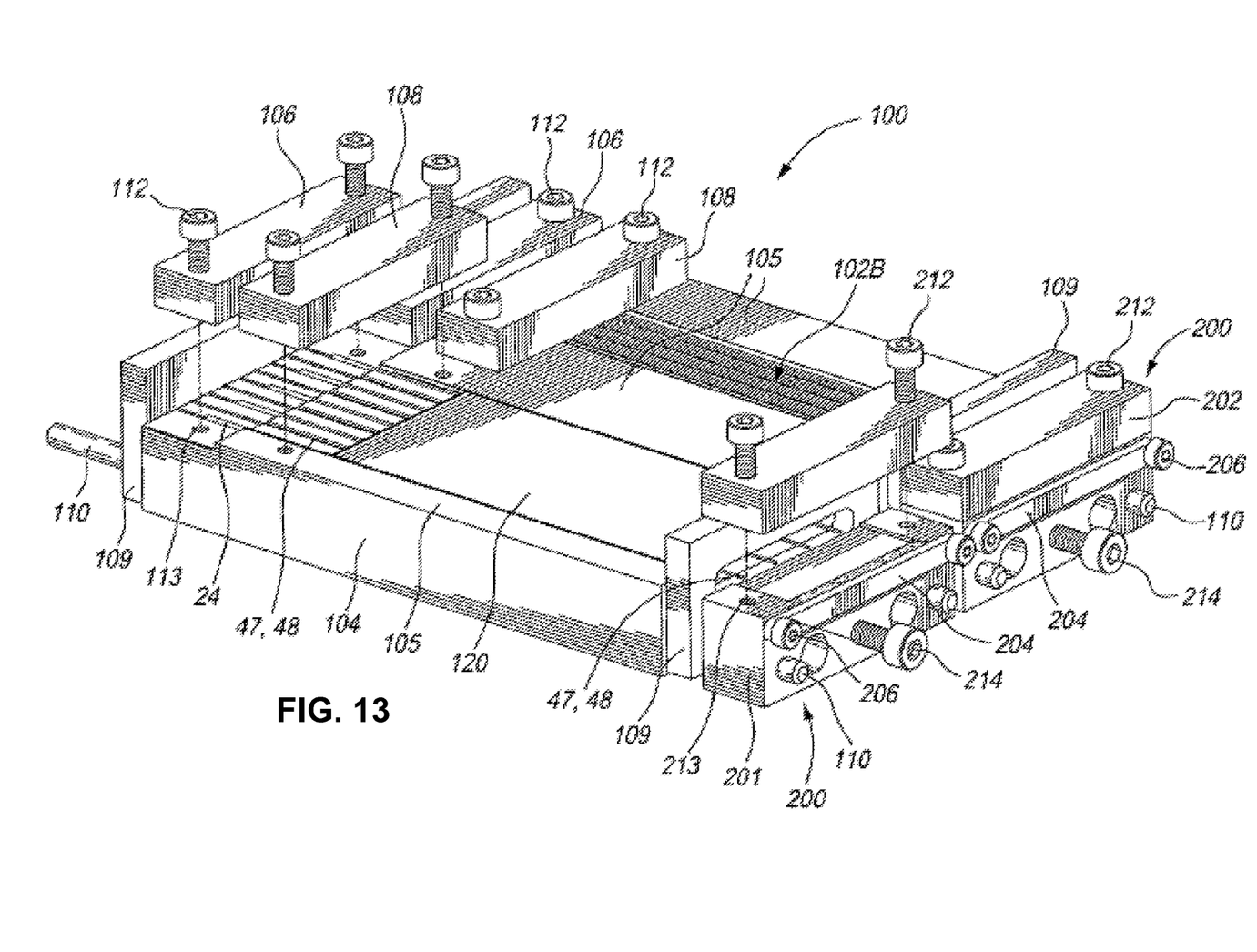
FIG. 13 is a perspective view of the apparatus of FIG. 5 showing the positioning of electrode wires.

Referring now to FIG. 13, the closing elements 24 tubing and ridges 31, 32, 33, 34 and 35 tubing are secured into their respective grooves 130a and 130b by the tubing clamps 108 and associated securing members 112. As for the electrode wires 41, 42, 43, 44, 45, 46, 47 and 48, they are aligned in their respective grooves 130c by having each of their ends pass through alignment holes 122 in the end plates 109, best seen in FIG. 9, secured at one end using wire clamps 106 and associated securing members 112, and their tightness adjusted using the tightness adjustment mechanism 200.

Figure 10:
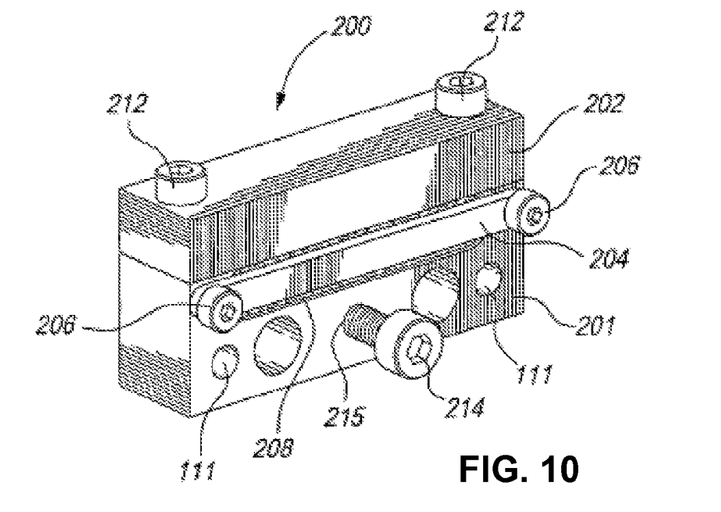
FIG. 10 is a perspective view of a tightness adjustment mechanism of the apparatus of FIG. 5.
Figure 11:
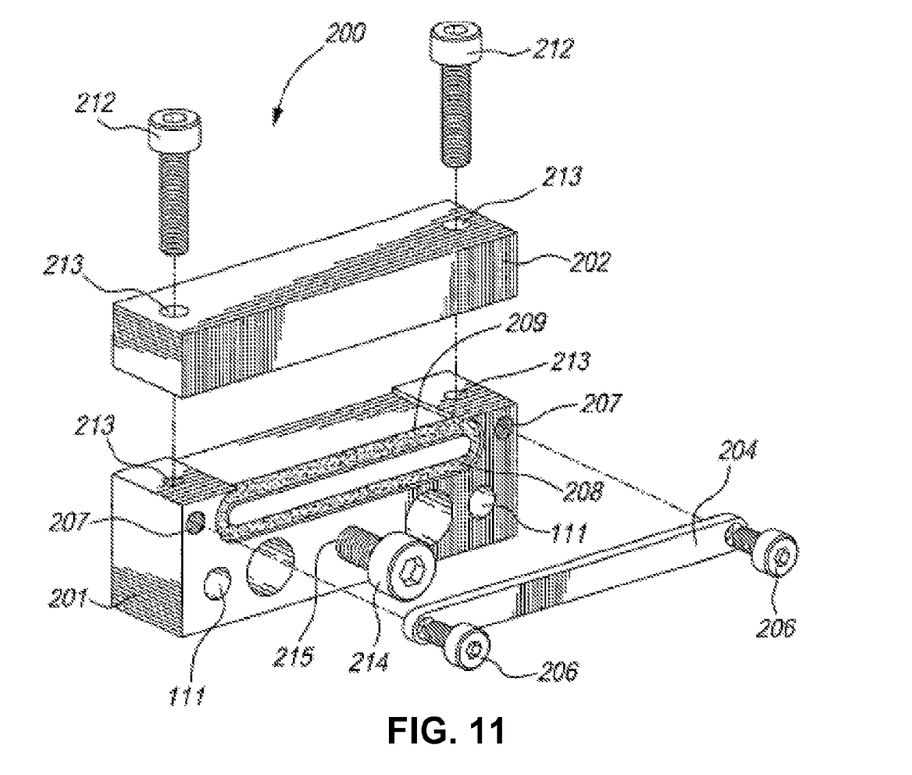
FIG. 11 is an exploded perspective view of the tightness adjustment mechanism of FIG. 10.

Referring to FIGS. 10 and 11, the tightness adjustment mechanism 200 includes a main body 201 and an electrode clamp 202, which may be secured to the main body 201 using associated securing members 212 and corresponding securing slots 213. Since the electrode wires 41, 42, 43, 44, 45, 46, 47 and 48 secured by the tightness adjustment mechanism 200 comprise part of the final product, 2 flexible silicone rubber plates are glued on the main body 201 and the electrode clamp 202, best seen in FIG. 6, to protect the electrode wires 41, 42, 43, 44, 45, 46, 47 and 48 when secured by the electrode clamp 202. The flexible silicone rubber plates made of high-consistency rubber (HCR) are cut in commercial implantable sheet grade from Allied Biomedical. When the electrode wires 41, 42, 43, 44, 45, 46, 47 and 48 are secured between the main body 201 and the electrode clamp 202, the tightness of the electrode wires 41, 42, 43, 44, 45, 46, 47 and 48 may be adjusted by rotating the tightness adjustment member 214. The tightness adjustment member 212, which is inserted in a threaded hole 215 within the main body 201, may be rotated until it enters in contact with the end plate 109, which displaces the tightness adjustment mechanism 200 away from the base 104 of the molding apparatus 100. The tightness adjustment member 214 may then be rotated, moving the tightness adjustment mechanism 200 farther away, until the desired tightness of the electrode wires 41, 42, 43, 44, 45, 46, 47 and 48 is achieved.

Figure 12:
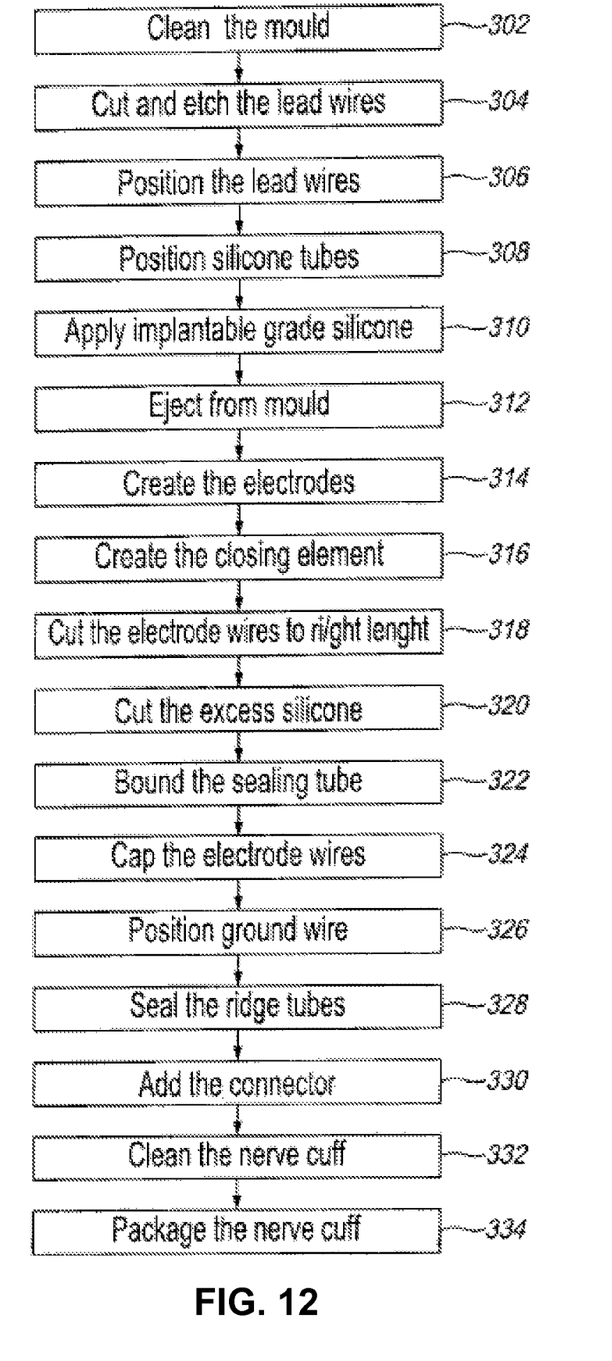
FIG. 12 is a flow diagram of the steps of a method of manufacturing a nerve cuff in accordance with an illustrative embodiment of the present invention.

The method for manufacturing of the nerve cuff 10 is depicted by the flow diagram shown in FIG. 12. The steps of the method are indicated by blocks 302 to 334. The method begins at block 302 where the mold is cleaned, for example with a 70% 2-propanol solution.

Then, at block 304, the electrode wires 41, 42, 43, 44, 45, 46, 47 and 48 are cut to appropriate lengths and etched. The etching ensures an appropriate adherence between the RTV silicone and ETFE coated electrode wires 41, 42, 43, 44, 45, 46, 47 and 48.

At block 306, the electrode wires 41, 42, 43, 44, 45, 46, 47 and 48 are inserted inside the alignment holes 122 of the end plates 109, which are then positioned such that the electrode wires 41, 42, 43, 44, 45, 46, 47 and 48 rest in their corresponding grooves 130c and secured to the base 104 of the molding apparatus 100 using the guiding members 110 and securing members 112. The strain of the electrode wires 41, 42, 43, 44, 45, 46, 47 and 48 is then adjusted with tightness adjustment mechanism 200.

At block 308, the closing elements 24 tubing and the ridges 31, 32, 33, 34 and 35 tubing are placed in their respective grooves 130a and 130b. Advantageously, small stainless steel rods may be positioned inside the closing elements 24 tubing and the ridges 31, 32, 33, 34 and 35 tubing in order to prevent movement during the molding process and insure their proper alignment. The electrode wire clamps 106 and tubing clamps 108 are then tightened, using their respective securing members 112, to prevent displacement of the closing elements 24 tubing, the ridges 31, 32, 33, 34 and 35 tubing and the electrode wires 41, 42, 43, 44, 45, 46, 47 and 48.

Then, at block 310, implant grade silicone 120, for example RTV silicone, is poured onto the mold 102 to form the wall member 20. The wall member 20 serves to adhere to and support the closing elements 24 along both edges of the nerve cuff 10, the ridges 31, 32, 33, 34 and 35 and the electrode wires 41, 42, 43, 44, 45, 46, 47 and 48. To ensure that the thickness of the wall member 20 is generally uniform throughout the nerve cuff 10, excess silicone is removed with, for example, a clean Teflon coated razor blade using flat surfaces 105, as may be seen in FIG. 13, on each side of the mold 102 as guides. Advantageously, the length of the mold 102 may be twice the length of the nerve cuff 10. This is to help stabilize the razor blade movement over the implant grade silicone 120 and provide a good surface finish. It is advantageous, in order to avoid flash (spilling), the blade is passed a second time hence, step 310 can be repeated which will result in a more consistent thickness.

At block 312, the wall member 20 is ejected from the mold 102. It is to be understood that the wall member 20 is not to be ejected from the mold 102 until a suitable amount of time has elapsed since the pouring of the implant grade silicone 120 to allow the implant grade silicone 120 to properly cure. This period of time may vary depending on the type of implant grade silicone 120 used, for example a period of 24 hours may be used in the case of RTV silicone.

At block 314, the electrodes (61a, 61b, 62), (63a, 63b, 64), (65a, 65b, 66) and (67a, 67b, 68) are created by removing lengths of ETFE insulation from the electrode wires 41, 42, 43, 44, 45, 46, 47 and 48. The ETFE insulation may be removed using, for example, a $CO_2$ TEA (transverse excited atmospheric) laser for a first rough pass followed by an Excimer laser to remove the thin layer of coating that may have been left by the $CO_2$ TEA, thus exposing the core 81 of the electrode wires 41, 42, 43, 44, 45, 46, 47 and 48. The indifferent electrodes (61a, 61b), (63a, 63b), (65a, 65b) and (67a, 67b) being positioned generally symmetrically at the extremities of the nerve cuff 10 while the recording electrodes are generally positioned in the center of the nerve cuff 10 with respect to its total length.

Then, at block 316, the closing elements 24 are cut from the closing elements 24 tubing using, for example, a Nd-Yag laser (or a $Co_2$ TEA laser) for example, such that the closing elements 24 on each side of the nerve cuff 10 form an interdigitating pattern such as shown in FIG. 2.

At block 318, the electrode wires 41, 42, 43, 44, 45, 46, 47 and 48 are cut using, for example, a Nd-Yag laser (or a $Co_2$ TEA laser) or cutters, such that they protrude beyond the desired length of the wall member 20 by approximately 2.0 mm.

At block 320, the unused portion of the wall member 20 is cut to the desired length using, for example, pliers, cutters and the like.

Then, at block 322, the sealing tube 25 is bound between one set of closing elements 24 and one of the ridges 31 or 35 tubing at the extremities of the nerve cuff 10 using, for example, implantable grade silicone. In the illustrative embodiment shown in FIG. 2, the sealing tube 25 is bound between one set of closing elements 24 and the tuning of ridge 35.

Figure 4A:
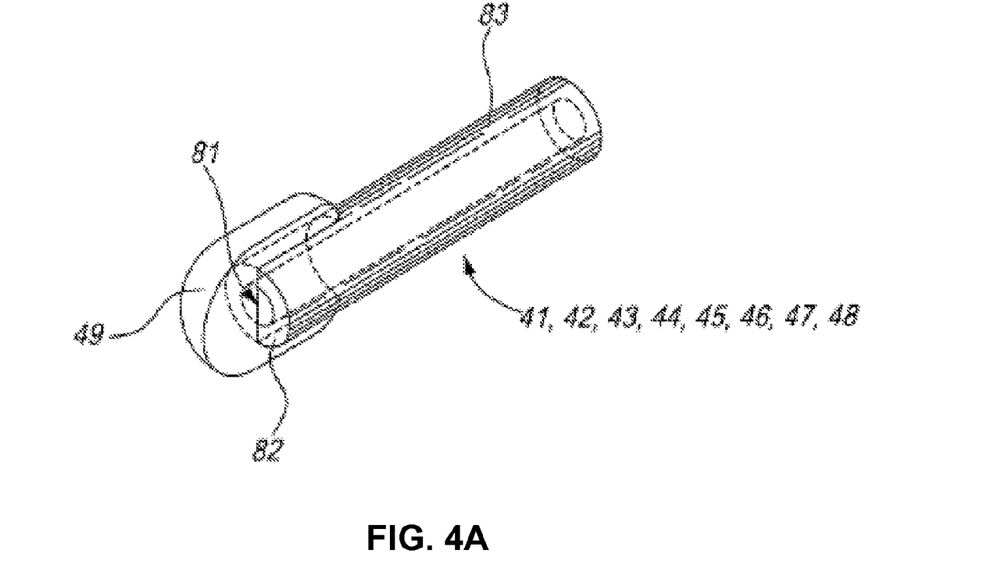
FIG. 4A is a perspective view of a capped electrode wire.
Figure 4B:
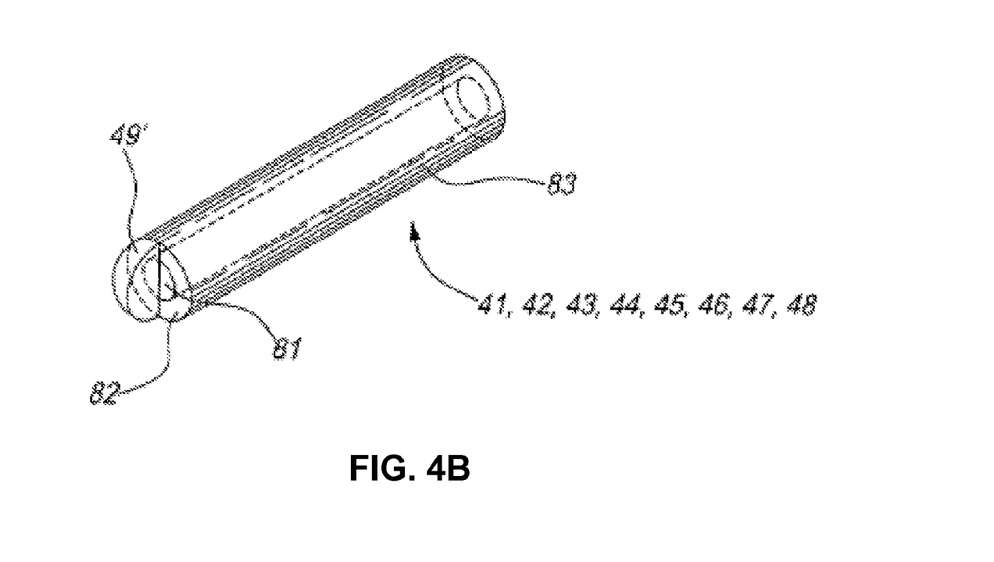
FIG. 4B is a perspective view of another embodiment of the capped electrode wire of FIG. 4A.

At block 324, the protruding ends of the electrode wires 41, 42, 43, 44, 45, 46, 47 and 48 are covered by implantable grade silicone, forming an electrode cap 49 as shown in FIG. 4A.

At block 326, the ETFE coating of the contact section 36b of the ground wire 36 is removed using, for example, a scalpel. The length of the contact section 36b will vary depending on the length of the nerve cuff 10. The contact section 36b of the ground wire 36 is then inserted inside the proximal end 33a of central ridge 33 tubing and follows the path defined previously in the description of the illustrative embodiment nerve cuff 10.

Then, at block 328, the proximal ends 31a, 32a, 33a, 34a and 35a and distal ends 31b, 32b, 33b, 34b and 35b of the ridges 31, 32, 33, 34 and 35 tubing are sealed with implantable grade silicone to prevent displacement of the ground wire 36. The implantable grade silicone introduced at each end of each ridge 31, 32, 33, 34 and 35 forms sealing caps 37 as shown in FIGS. 1 and 2.

At block 330, a connector (not shown) may be connected to the contact section 36b of the ground wire 36 and to the electrode wires 41, 42, 43, 44, 45, 46, 47 and 48 for connection of the nerve cuff 10 to some further interface or device (not shown).

At block 332, the nerve cuff 10 is cleaned with, for example, a 70% 2-propanol solution and, at block 234, it is package sterile packaging for storage or shipment.

Although the present invention has been described by way of particular embodiments and examples thereof, it should be noted that it will be apparent to persons skilled in the art that modifications may be applied to the present particular embodiment without departing from the scope of the present invention.

What is claimed is:

1. A method of manufacturing a nerve cuff, the method comprising the steps of:
    (a) providing a mold comprising a plurality of longitudinal grooves;
    (b) positioning one of a plurality of longitudinal conductors coated with insulation within each longitudinal groove;
    (c) applying flexible bio-compatible material on the mold with the plurality of longitudinal conductors positioned therein;
    (d) curing the flexible bio-compatible material so as to provide a wall band member with the plurality of longitudinal conductors adhered thereto;
    (e) ejecting the wall band member with the adhered plurality of longitudinal conductors; and
    (f) removing at least one portion of the insulation on the plurality of longitudinal conductors to provide electrodes, wherein each of the at least one portions is situated between a proximal end and a distal end of each longitudinal conductor.

2. The method of claim 1, wherein step (b) further comprises positioning one of a plurality of longitudinal tubes within each of the longitudinal groove, step (c) comprises applying the flexible bio-compatible material on the mold with the plurality of longitudinal conductors and the plurality of longitudinal tubes positioned therein, step (d) comprises curing the flexible bio-compatible material so as to provide a wall band member with the plurality of longitudinal conductors and the plurality of longitudinal tubes adhered thereto; and step (e) comprises ejecting the wall band member with the adhered plurality of longitudinal conductors and plurality of longitudinal tubes.

3. The method of claim 2, wherein the plurality of longitudinal tubes are made of silicone.

4. The method of claim 2, wherein each of a plurality of rods are positioned in each longitudinal tube before step (b).

5. The method of claim 2, wherein after curing, the plurality of longitudinal tubes comprise ridge tubes for providing ridges along the length of the wall band member.

6. The method of claim 5, wherein each longitudinal groove having the conductor positioned therein provide the electrodes at substantially the same level as the top of the ridges.

7. The method of claim 5, wherein after ejecting, a ground wire is inserted through each of the ridges via a respective proximal and distal end of each ridge.

8. The method of claim 7, wherein after inserting the ground wire, the ridges are sealed at their respective proximal and distal ends.

9. The method of claim 7, further comprising connecting a connector to the longitudinal conductor and the ground wire to provide further interface.

10. The method of claim 2, wherein after curing, each longitudinal tube comprises one of a plurality of closing element tubes to provide a closing element positioned at each of two lateral sides of the wall band member.

11. The method of claim 10, wherein portions of each of the plurality of closing elements are removed to provide two sets of closing elements, each set situated at one of the two lateral sides of the wall band member, wherein the set of closing elements situated at one lateral side form a mutually engaging interdigitating pattern with the set of closing elements situated at an opposite lateral side when the nerve cuff is in a closed position.

12. The method of claim 11, further comprising binding a sealing tube to the set of closing elements situated at the one lateral side and a ridge to the set of closing elements situated at the opposite lateral side of the wall band member.

13. The method of claim 1, wherein the longitudinal conductors protrude beyond the longitudinal grooves when positioned therein, the method further comprising cutting the protruding ends of the conductors to a desired length.

14. The method of claim 13, further comprising applying flexible bio-compatible material on the remaining protruding ends of the conductors to cap the conductors.

15. The method of claim 1, wherein each conductor comprises a pair of insulated wires.

16. The method of claim 15, wherein before positioning the conductors in the longitudinal grooves, the wires are cut to appropriate length and etched so as to facilitate adherence to a bio-compatible material after curing thereof.

17. The method of claim 1, wherein after ejecting, the excess material of the wall band member is removed.

18. The method of claim 1, wherein the flexible bio-compatible material comprises silicone.

* * * * *